United States Patent
Klassen et al.

(10) Patent No.: US 6,820,023 B1
(45) Date of Patent: Nov. 16, 2004

(54) AUTOMATED ULTRASONIC INSPECTION PLANNING

(75) Inventors: Allen Anthony Klassen, Loveland, OH (US); Joseph Charles Zambito, Cincinnati, OH (US); Paul Stephen Manicke, West Chester, OH (US); Robert John McElligott, Loveland, OH (US); Catherine Mary Graichen, Malta, NY (US); Christopher Reynolds Hammond, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 5 days.

(21) Appl. No.: 09/685,260

(22) Filed: Oct. 10, 2000

(51) Int. Cl.[7] .............................................. G01N 29/06
(52) U.S. Cl. ....................................................... 702/83
(58) Field of Search ............................... 702/83, 51, 95; 73/600, 621, 602, 622, 610, 606, 866, 623, 866.5, 633; 359/505, 565; 250/559; 356/497, 638; 318/569; 700/110; 378/207; 364/571, 551, 413.25; 395/143, 162; 707/901; 367/13

(56) References Cited

U.S. PATENT DOCUMENTS

| | | | | |
|---|---|---|---|---|
| 4,757,716 A | * | 7/1988 | Nottingham et al. ......... 73/623 |
| 4,945,501 A | * | 7/1990 | Bell et al. ..................... 318/632 |
| 5,146,432 A | * | 9/1992 | Kimball et al. ................. 367/13 |
| 5,208,747 A | * | 5/1993 | Wilson et al. ................. 600/443 |
| 5,297,256 A | * | 3/1994 | Wolstenholme et al. ....... 700/83 |
| 5,331,855 A | * | 7/1994 | Takashita et al. .............. 73/602 |
| 5,384,905 A | * | 1/1995 | Tanaka et al. ................. 345/442 |
| 5,531,855 A | * | 7/1996 | Heinecke et al. ............. 156/248 |
| 5,549,002 A | * | 8/1996 | Howard et al. ................. 73/602 |
| 5,659,491 A | * | 8/1997 | Ichikawa et al. ............. 700/112 |
| 6,070,177 A | * | 5/2000 | Kao et al. ....................... 707/10 |
| 6,200,025 B1 | * | 3/2001 | Rich ........................... 378/207 |
| 6,220,099 B1 | * | 4/2001 | Marti et al. .................... 73/633 |
| 6,279,397 B1 | * | 8/2001 | Dwyer ........................... 73/606 |
| 6,327,921 B1 | * | 12/2001 | Hsu et al. ................... 73/866.5 |
| 6,549,820 B1 | * | 4/2003 | Barrett et al. ................ 700/110 |

* cited by examiner

*Primary Examiner*—John Barlow
*Assistant Examiner*—Tung Lau
(74) *Attorney, Agent, or Firm*—William Scott Andes; Armstrong Teasdale LLP (57) ABSTRACT

A method for automatically generating an ultrasonic inspection plan for parts to be inspected includes collecting data relating to the ultrasonic inspection planning by displaying an input screen that prompts a user to input the pertinent data. The inspection parameters to be used in the ultrasonic inspections are then calculated from the collected data, and the calculated parameters are formatted into an inspection plan document. A tool for carrying out this method can be implemented on any computer-readable medium.

39 Claims, 5 Drawing Sheets

AUTOMATED ULTRASONIC INSPECTION PLANNING

BACKGROUND OF THE INVENTION

This invention relates generally to ultrasonic inspection and more particularly to automatically generating ultrasonic inspection planning.

Ultrasonic inspection is a commonly used technique to inspect various manufactured parts for defects. In particular, ultrasonic inspection is a primary method of identifying processing and melt-related defects in rotating components used in jet engines. In the manufacture of such rotating component parts, a billet of the raw material, such as titanium, used to manufacture the part is formed from a cropped cylindrical ingot. The billets are cut into a series of pieces called mults, and each piece is forged into a "sonic shape" forging that approximates the desired shape of: the part. The forgings are subsequently machined to form the finished part.

It is common to ultrasonically inspect the sonic shape forging for defects prior to the final machining process. To conduct an inspection, the forging is ordinarily immersed in water or another fluid and rotated about its center axis, and the surfaces of the forging are scanned with one or more ultrasonic transducers. The transducers emit pulses of ultrasonic energy that impinge on the forging and receive ultrasound waves reflected from the forging. The reflected waves are electronically processed into signals that can be displayed as a two-dimensional image, from which representations of defects and flaws can be identified.

Normally, an ultrasonic inspection plan is developed for each part design to insure that the forgings are fully and consistently inspected. Developing such an inspection plan involves determining inspection parameters such as the speed (in RPM) at which the forging will be rotated, the surface speed of the forging, how fast the transducer will be indexed with respect to the forging, pulse repetition rate and scan length. Typically, these parameters are manually calculated using a standard set ultrasonic inspection planning formulas. However, this process often requires many calculations (typically about 200–300), and is thus time consuming and increases the possibility of one or more errors.

Furthermore, it is not uncommon for part forgings to be provided by more than one forging shop or supplier. In this case, each supplier generally develops its own ultrasonic inspection planning, which is then reviewed and approved by the customer. This results in a multitude of inspection planning formats that require extensive review for approval. This approach can also produce inspection variability from site-to-site, which causes inconsistent inspection results.

Accordingly, there is a need for a method and means for generating ultrasonic inspection planning on a quick, consistent basis.

BRIEF SUMMARY OF THE INVENTION

The above-mentioned need is met by the present invention, which provides a method and a tool for automatically generating an ultrasonic inspection plan for a part. The invention includes collecting data relating to the ultrasonic inspection planning by displaying an input screen that prompts a user to input the pertinent data. The inspection parameters to be used in the ultrasonic inspections are then calculated from the collected data, and the calculated parameters are formatted into an inspection plan document. The tool can be implemented on any computer-readable medium.

The present invention and its advantages over the prior art will become apparent upon reading the following detailed description and the appended claims with reference to the accompanying drawings.

BRIEF DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Referring to the drawings wherein identical reference numerals denote the same elements throughout the various views, the present invention includes a method and a tool (referred to herein as an ultrasonic inspection planning generator) for generating ultrasonic inspection planning for parts to be inspected. In one preferred embodiment, the ultrasonic inspection planning generator is implemented as a file in a spreadsheet software application. The software application could be any spreadsheet application including commercially available spreadsheet applications such as Microsoft Excel. The spreadsheet file is configured to accept part related inputs from a user and then run a set of macros to generate a standardized set of inspection planning for the part involved. The inspection planning contains all of the information (e.g., part nomenclature, standard instructions, inspection coverage, inspection zone sketch, inspection sequence, equipment parameters and revision history) needed to meet specification requirements.

Figure 1:
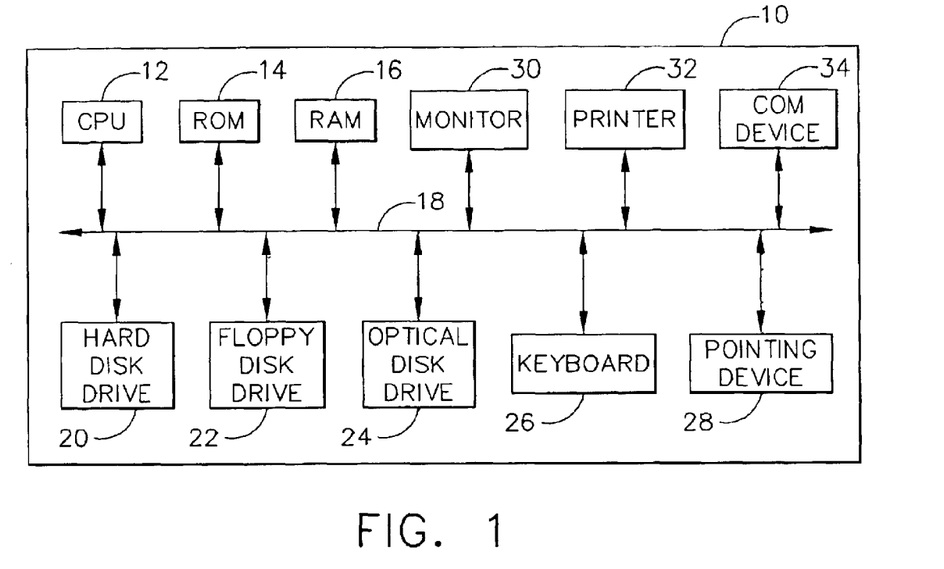
FIG. 1 is a block diagram of one exemplary computer system implementing the ultrasonic inspection planning generator of the present invention.

FIG. 1 illustrates an exemplary computer system 10, on which the present invention can be implemented. The computer system 10 is a personal or work station computer that includes a central processing unit (CPU) 12, which can be any type of microprocessor or other known processor, a read only memory (ROM) 14 and a random access memory (RAM) 16 connected by a system bus 18. The system bus 18 may be any of several types of bus structures and may actually comprise multiple bus structures interconnected by various bridges, adapters and/or controllers. The computer system 10 also includes a hard disk drive 20 for reading from and writing to a hard disk (not shown), a floppy disk drive 22 for reading from or writing to a floppy disk, and an optical disk drive 24 for reading from or writing to an optical disk such as a CD-ROM or other optical media. The hard disk drive 20, floppy disk drive 22, and optical disk drive 24 are connected to the system bus 18 by conventional interfaces (not shown).

Although the exemplary computer system 10 as described herein employs drives for hard disks, floppy disks and optical disks, it should be appreciated by those skilled in the art that other types of computer readable media, such as magnetic tapes, might also be used. Also coupled to the system bus 18 are known input/output devices such as a keyboard 26, a pointing device 28, a monitor 30 and a printer 32. A communication device 34, such as a modem, is included for providing the computer system 10 with a connection to a computer network such as the Internet, a wide area network (WAN) or a local area network (LAN). While one exemplary computer system has been described herein, those skilled in the art will appreciate that the present invention can be implemented on other types of computer systems such as a multiprocessor systems, main frame computers, portable computers and the like.

To utilize the inspection planning generator, a user accesses the spreadsheet file with the computer system 10. This can be accomplished in a number of ways. For instance, the spreadsheet file could be downloaded (typically onto the hard disk) from a remote computer system via the Internet or other computer network through the communication device 34. Alternatively, the spreadsheet file could be accessed from a removable computer-readable medium, such as a floppy disk or a CD-ROM inserted into the floppy disk drive 22 or optical disk drive 24, respectively. With this approach, the spreadsheet file could be accessed directly from the removable computer-readable medium, or it could be transferred to the hard disk and accessed from there. As used herein, the term "computer-readable medium" refers generally to any medium from which stored data can be read by a computer. This includes not only removable media such as the aforementioned floppy disk or CD-ROM, but also non-removable media such as the hard disk.

Figure 2:
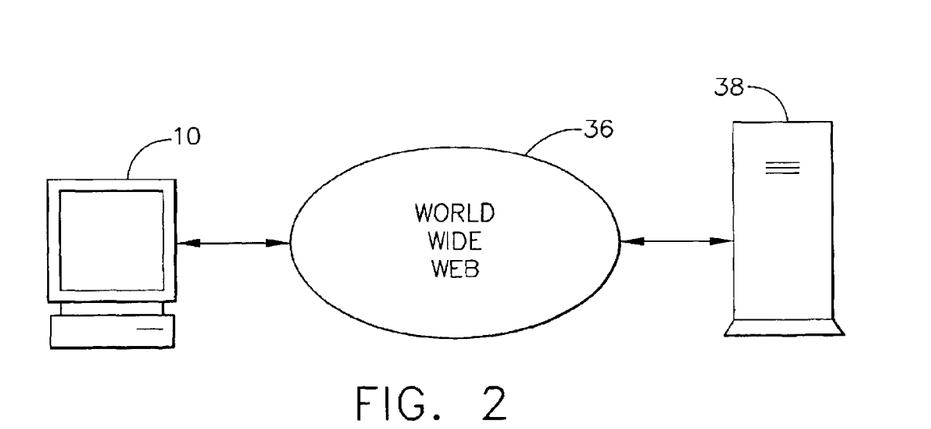
FIG. 2 is a block diagram of a distributed system for implementing the ultrasonic inspection planning generator.

In an other alternative, the spreadsheet file could be implemented as a web-based tool that is not transferred onto the computer system 10, but is instead stored on another computer system and accessed with the computer system 10. For example, FIG. 2 shows an arrangement in which the computer system 10 is connected to another computer system 36 via the World Wide Web computer network 38. In this case, the user computer system 10 includes a conventional web browser software application that allows the computer system 10 to access Hypertext Markup Language (HTML) web pages and other data stored on the second computer system 36. The second computer system 36 includes a web server (i.e., a computer program that serves requested HTML pages or files) and has the spreadsheet file stored in its memory. Thus, a user is able to access and launch the spreadsheet file by inputting the appropriate Internet address or selecting the appropriate link on a web page. With this arrangement, the spreadsheet file can also be accessed by other users at other locations using computer systems similar to the computer system 10. This provides a distributed system that is capable of uniform distribution of the ultrasonic inspection planning generator to a number of sites. It should be noted that distributed systems making use of computer networks other than the World Wide Web (e.g., the Internet generally, WANs and LANs) are also encompassed by the present invention.

Figure 3:
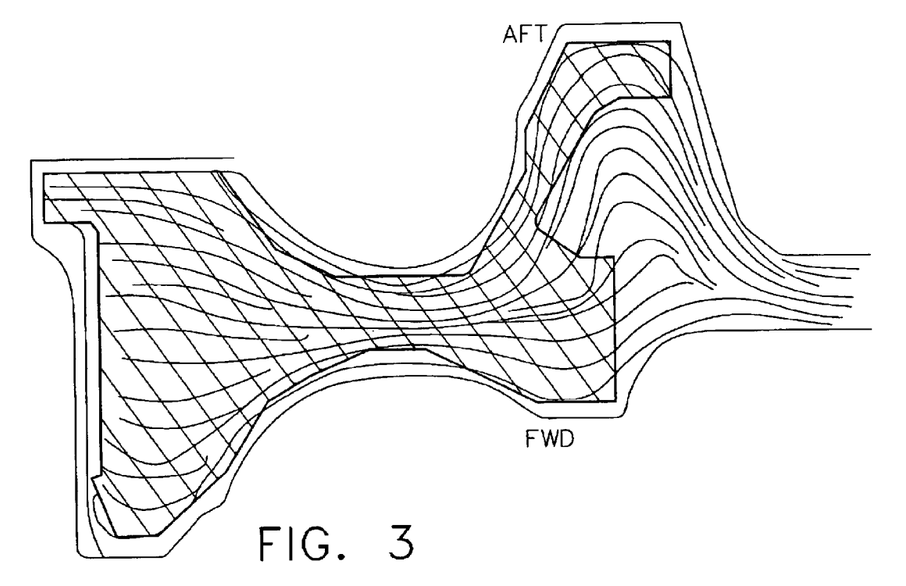
FIG. 3 is an exemplary flow line plot of a fan disk.
Figure 4:
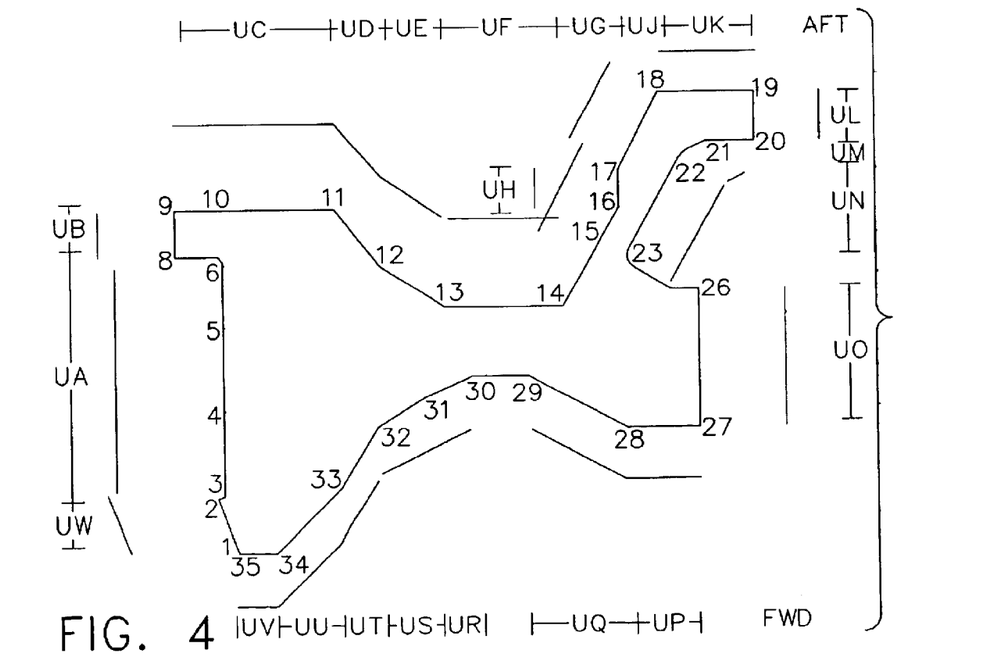
FIG. 4 is an exemplary scan line plot of a fan disk.

Once the file is launched, a spreadsheet screen is displayed on the monitor 30. The spreadsheet screen includes two user interface sheets: an instruction sheet and an input sheet. (The spreadsheet screen includes additional sheets that are described below.) The instruction sheet, which is initially displayed on the monitor 30, shows the prerequisites for using the inspection planning generator and a set of instructions for generating a set of ultrasonic inspection planning. The prerequisites include a flow line digital image of the part for which the ultrasonic inspection planning is being generated, a scan line digital image of the part and geometry data for the part. The digital images are typically TIFF files and can be stored on the hard disk of the computer system 10. The flow line image shows the sonic shape, finished part shape, forging flow lines and inspection coverage of the part. The scan line image shows the sonic shape of the part with ultrasonic areas, scans and geometry points. Exemplary flow line and scan line images of a stage 1 fan disk for a jet engine are shown in FIGS. 3 and 4, respectively. While the present invention is particularly useful for generating inspection planning for jet engine rotating components, it is not so limited and can be applied to a large number of parts.

The part geometry data is defined by the radius and height of points around the cross section of the part. The radius is from the part centerline and the height is from the surface on which the part rests. The points are to be defined moving in a counterclockwise direction around the part when looking at the right side of the centerline. Preferably, the points define all inspection points as a minimum. The prerequisites further include the current revision sheet for the part, ultrasonic transducer data for all zones to be used for part inspection, and a proposed sequence of inspection scans to be performed. The proposed sequence of inspection scans is developed by the user in accordance with the specification requirements for the part.

After reviewing the instruction sheet and obtaining the prerequisites, the user calls up the input sheet (shown in FIGS. 5–8) by clicking the pointing device 28 on the input tab 40 near the bottom of the spreadsheet, thereby causing the input sheet to be displayed on the monitor 30. The input sheet is a graphical user interface that guides the user through the ultrasonic inspection planning process as will now be described. The input sheet contains a number of different data input sections that elicit different types of data related to the inspection planning process.

Figure 5:
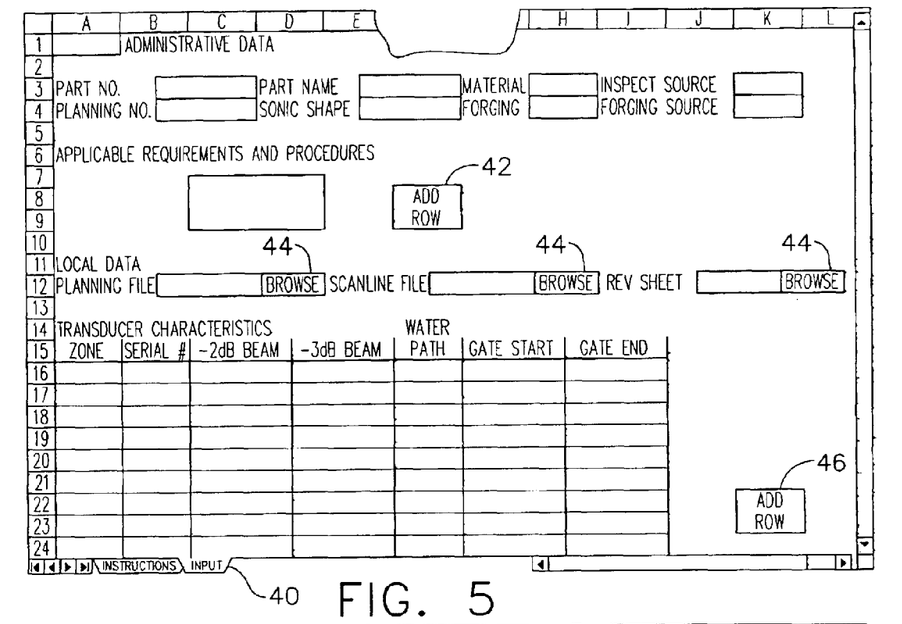
FIGS. 5–8 graphically illustrate different sections of a data input screen of the present invention.

FIG. 5 shows the first four data input sections: an Administrative Data section, an Applicable Requirements and Procedures section, a Local Data Source section and a Transducer Characteristics section. In the Administrative Data section, the user is prompted to enter general, administrative data such as part number, planning number, part name, type of material the part is made of, the forging source, the inspection source and the revision number. A number of fields or input windows are included in which the appropriate data are entered. In the Applicable Requirements and Procedures section, the user is able to input the local shop procedures that will apply to the inspection. An Add Row button 42 is included in this section. Selecting this button 42 will run a macro that will add a blank row to the end of the Applicable Requirements and Procedures section. Thus, the user can use Add Row button 42 to add input rows as needed. The Local Data Source section includes input windows for the user to identify the file locations for the flow line digital image, the scan line digital image and the revision sheet. These files are typically located on the hard drive of the computer system 10, although they could also be stored on a network, if the computer system 10 is networked. A Browse button 44 is provided with each file entry to enable the user to browse for and find the appropriate file and thereby store the file in the corresponding cell in the spreadsheet file. In the Transducer Characteristics section, the pertinent characteristics of the transducer to be used in the inspection are inputted. For each zone to be used for part inspection, the serial number, the 2 dB beam width, the −3 dB beam width, the water path, the gate start and the gate end data are entered. Like the Applicable Requirements and Procedures section, the Transducer Characteristics section includes an Add Row button 46 for allowing the user to add input rows as needed.

Figure 6:
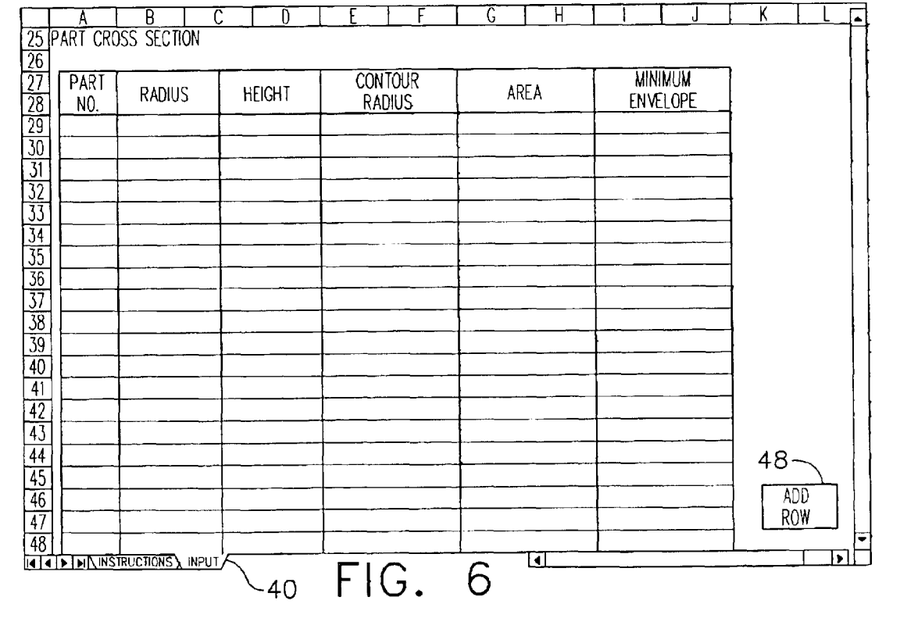

FIG. 6 shows a Part Cross Section section in which the part geometry data is input. This section contains an array of input windows in which the user enters the part geometry data. For each point, the user enters the part radius, part height, radius of any concave contours, ultrasonic area and minimum envelope. This section includes another Add Row button 48 for adding input rows if needed.

Figure 7:
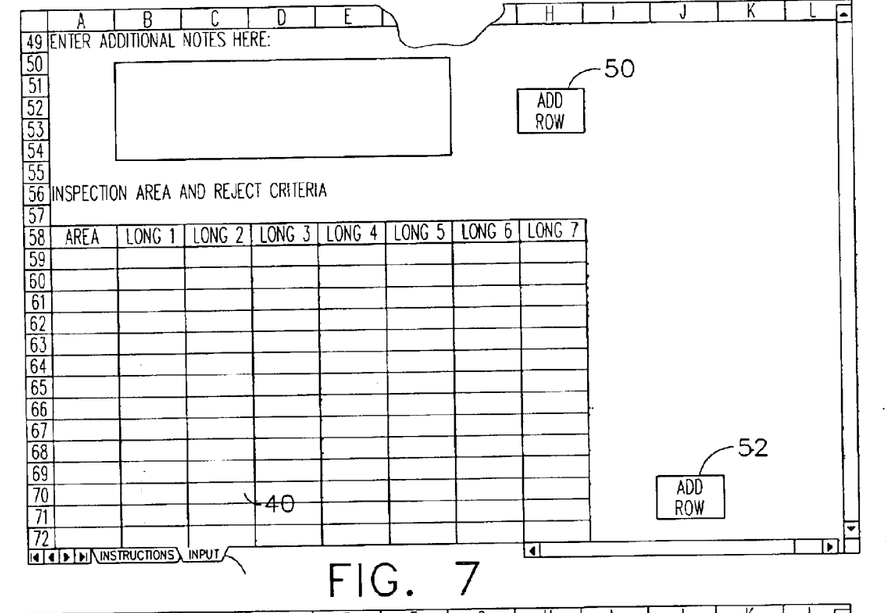

FIG. 7 shows two more data input sections: an Additional Notes section and an Inspection Area Definition and Reject Criteria section. The Additional Notes section provides an input window in which the user can input any additional inspection requirements such as angulation for inspection coverage, special gating requirements, and sonic shape drawing number. Again, an Add Row button 50 is provided for adding input row to the end of the Additional Notes section. In the Inspection Area Definition and Reject Criteria section, the user enters information to define what areas and zones of the part are to be inspected. Specifically, the user enters the reject amplitude for the pertinent zones in each area. The user selects these inputs based on the general inspection requirements. This section also includes an Add Row button 52 for adding additional input rows.

Figure 8:
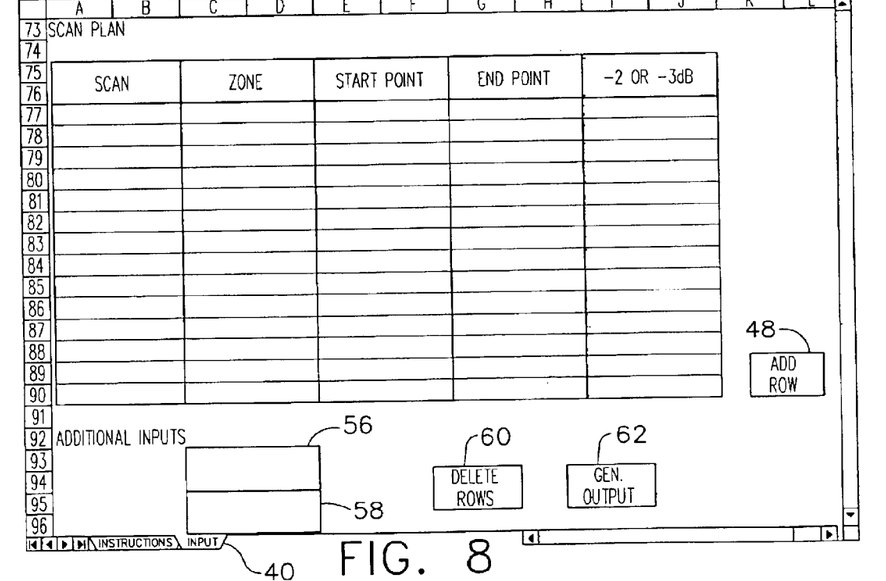

Lastly, FIG. 8 shows a Scan Plan section and an Additional Inputs section. In the Scan Plan section, the user inputs the previously determined proposed sequence of scans for the inspection. This comprises a number of scans wherein the zone, start point, end point and beam width for each scan is defined. Another Add Row button 54 is provided for adding additional input rows. To insert input rows, the spreadsheet protection should be turned off. The spreadsheet protection can be reactivated when the scan sequence entry is completed. The Additional Inputs section contains an input box 56 relating to pulse on position capability. If the inspection equipment being used has this capability, then the user enters YES in this box 56. If not, then: the user enters NO in the box 56. The Additional Inputs section contains a second input box 58 in which the user is able to input an estimate of the time needed to load, inspect and unload a part.

At this point, the data input process is completed, and the user next clicks on a Delete Blank Rows button 60 that is located at the end of the input sheet. Selecting the Delete Blank Rows button 60 will initiate a macro in the spreadsheet file that eliminates blank rows in each data input section of the input sheet. The user also opens a word processing software application on the computer system 10. The system is now ready to generate an ultrasonic inspection planning. To do so, the user clicks on a Gen Output button 62 that is also located at the bottom of the input sheet. This initiates an overall control macro in the spreadsheet file that performs calculations using the data inputted at the input sheet and generates an ultrasonic inspection planning for the part that is output as a word processing document. The control macro calculates the part RPM, part surface speed, transducer index speed, pulse repetition rate and scan length from the input data using standard ultrasonic inspection planning formulas that are embedded into the macro. The control macro also generates an error proofing plot of the part cross section that is printed on the printer 32. The user compares the error proofing plot to the actual part cross section to verify that the part geometry data was inputted correctly. In other words, if the error proofing plot does not adequately resemble the part cross section, then the user will know that one or more errors were made inputting the part geometry data.

The calculated results and other data are formatted into a completed inspection plan document, which as stated above is a word processing document. The user then prints the completed inspection plan document on the printer 32. The inspection plan document is then submitted for engineering approval, after which the inspection planning can used by an ultrasonic inspector for conducting part inspections.

Figure 9:
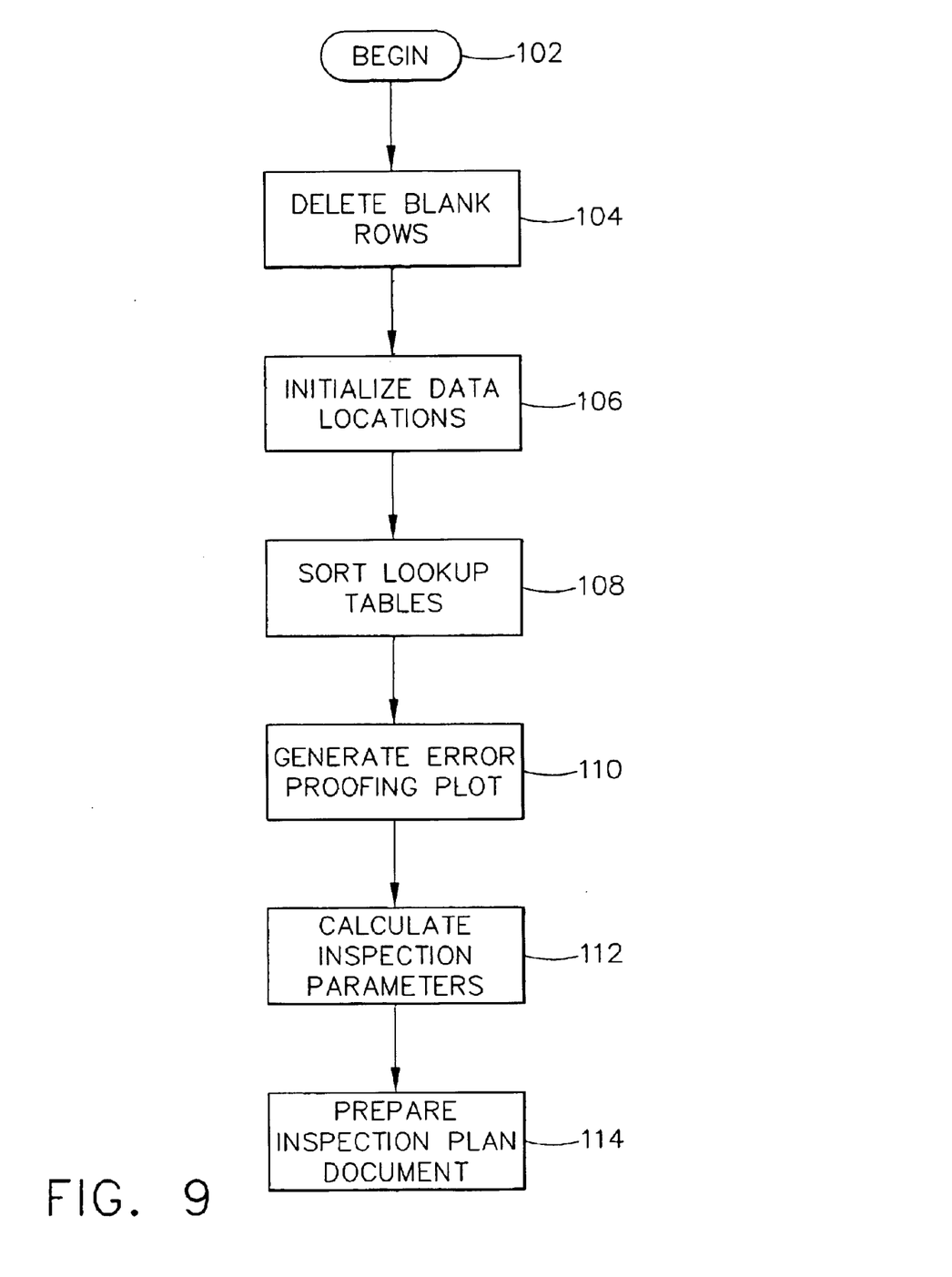
FIG. 9 is a flow chart illustrating an ultrasonic inspection planning process.

Referring to FIG. 9, a more detailed description of the operation of the overall control macro is provided. The macro begins at block 102. As indicated above, this occurs when the user selects the Gen Output button 62 on the bottom of the input sheet. The next step, at block 104 is to delete all blank rows in the input sheet portion of the spreadsheet. This step is included in the overall control macro in case the user neglected to select the Delete Blank Rows button 60 prior to selecting the Gen Output button 62. At block 106, the control macro initializes data locations by setting up references to columns, rows and cells for the data in each of the data input sections. Also, the control macro adjusts the section row counts in accordance with the size of the data inputs for each section.

At block 108, the control macro sorts the input data into lookup tables by a key field, such as name. The data are sorted in such a manner (e.g., alphabetically) so as to insure lookup functions will execute properly. Next, the error proofing plot is generated as indicated at block 110. This is accomplished by copying the part geometry data from the Part Cross Section data input section to a plot sheet. As mentioned above, the error proofing plot is outputted so that the user can verify that the part geometry data was inputted correctly. This step also includes creating a named reference to the plot data and updating the plot data source to a new data range.

At block 112, the macro calculates the inspection parameters that will go into the ultrasonic inspection planning. First, selected data collected from the input sheet, referred to herein as the scan input data, is copied to a calculation sheet. Because of the potential loss of inspection sensitivity associated with curved surfaces, the macro provides automatic adjustments to the scan input data based on curvature corrections. This is done by looking at the part geometry data to identify any convex surfaces of a predetermined severity (such as a radius of curvature less than 4 inches). For each such surface identified, the macro then goes to a correction lookup table to find the appropriate curvature correction. The lookup table stores corrections based on the type of transducer being used, the radius of curvature and the depth of inspection.

Next, inspection parameters are calculated from the scan input data and the plot data references created at block 110. The inspection parameters include part RPM, part surface speed, transducer index speed, pulse repetition rate and scan length and are calculated using standard ultrasonic inspection planning formulas that are embedded into the control macro. Using the calculated results and the other data such as the number of scans to be conducted, the number of zones that are being calibrated on, scanning time and shop factor, the time to perform the inspection is also calculated. All of the results are formatted for insertion into the completed inspection plan document as a sequence of inspection scans. Lastly, the macro parses the scan sequence to verify that all scans dictated by specification requirements have been included. If any scan is missing, the process is stopped and an error message is sent out. The missing line or lines in the scan sequence sheet are highlighted. The user goes back to the input sheet and enters the missing data and then clicks the Gen Output button 62 again to restart the overall control macro.

The completed inspection plan document is prepared at block 114 using the calculated inspection parameters and other data collected from the input sheet. First, a new file in the word processing application is created to be the inspection plan document. The document is then subjected to a page setup to set the margins, fonts, styles, etc. The next step is to insert the local shop procedures from the Applicable Requirements and Procedures section of the input sheet into the inspection plan document. Also, a standard set of comments and rules that are applicable to all ultrasonic inspection plans is inserted into the inspection plan document. Then, the control macro finds the specified file from the flow line cell and copies the flow line digital image into the inspection plan document. The control macro also finds the specified file from the scan line cell and copies the scan line digital image picture into the inspection plan document. If a scan line file has not been specified, the basic plot shape from the Part Cross Section data input section is copied into the document. The next step is to copy and format the inspection input data from the Inspection Area Definition and Reject Criteria section and the notes input from the Additional Notes section into the inspection plan document. The control macro then formats the scan input data and the calculated results from the calculation sheet into an inspection scan sequence and copies this into the inspection plan document. The macro will then find the specified file from the revision sheet cell and insert it into the inspection plan document. Lastly, the macro creates and formats a page header for the inspection plan document using the administrative data input from the Administrative Data section.

The completed inspection plan document in comprises a sequence of inspection scans to be performed, including the zone, area, part RPM, part surface speed, transducer index speed, pulse repetition rate and scan length for each scan. The inspection plan document also includes a page header containing administrative data, inspection requirements and standard comments, flow line and scan line sketches of the part, inspection limits, notes and the revision history of the part.

The foregoing has described a method and means for automatically generating ultrasonic inspection planning. The present invention is able to greatly reduce the amount of time required to generate an inspection planning. In addition, the inspection planning is more consistent among different sites or operations as the planning methodology between sites will be more uniform.

While specific embodiments of the present invention have been described, it will be apparent to those skilled in the art that various modifications thereto can be made without departing from the spirit and scope of the invention as defined in the appended claims.

What is claimed is:

1. A method of using a computer to generate an ultrasonic inspection planning for a part, said ultrasonic inspection planning containing information needed to meet specification requirements for an ultrasonic inspection, said method comprising:

collecting data relating to said ultrasonic inspection planning, said data including part geometry data and a revision sheet for said part;

using said data to calculate inspection parameters; and outputting a set of inspection planning based on said calculated parameters.

2. The method of claim 1 wherein said data further includes a flow line image and a scan line image for said part.

3. The method of claim 1 wherein said data further includes ultrasonic transducer characteristics.

4. The method of claim 1 further comprising generating an error proofing plot of said part and comparing said error proofing plot to a cross section drawing of said part.

5. The method of claim 1 wherein using said data to calculate inspection parameters includes calculating one or more of part rotational speed, part surface speed, transducer index speed, pulse repetition rate and scan length.

6. The method of claim 1 wherein said inspection plan document sets forth a sequence of inspection scans for said part.

7. The method of claim 1 further comprising adjusting said data for part curvature corrections.

8. The method of claim 6 wherein said document further includes a flow line image, a scan line image, inspection limits and a revision history for said part.

9. The method of claim 6 further comprising parsing said sequence of inspection scans to verify that all required scans are included.

10. A method for automatically generating an ultrasonic inspection planning for a part, said ultrasonic inspection planning containing information needed to meet specification requirements for an ultrasonic inspection, said method comprising:

displaying an input screen for prompting a user to input data relating to said ultrasonic inspection planning;

calculating inspection parameters from said data; and formatting said calculated parameters into an inspection plan document that sets forth a sequence of inspection scans for said part said document including a flow line image, a scan line image, inspection limits and a revision history for said part.

11. The method of claim 10 further comprising displaying an instruction screen.

12. The method of claim 10 further comprising generating an error proofing plot of said part.

13. The method of claim 10 wherein calculating inspection parameters includes calculating one or more of part rotational speed, part surface speed, transducer index speed, pulse repetition rate and scan length.

14. The method of claim 10 further comprising parsing said sequence of inspection scans to verify that all required scans are included.

15. The method of claim 10 further comprising adjusting said data for part curvature corrections.

16. The method of claim 10 wherein said data includes part geometry data for said part.

17. The method of claim 16 wherein said data further includes a flow line image and a scan line image for said part.

18. The method of claim 16 wherein said data further includes a revision sheet for said part.

19. The method of claim 16 wherein said data further includes ultrasonic transducer characteristics.

20. The method of claim 16 wherein said data further includes a proposed sequence of inspection scans.

21. A computer-readable medium containing instructions for controlling a computer system to perform a method comprising:

displaying an input screen for prompting a user to input data relating to an ultrasonic inspection planning for a pail, said ultrasonic inspection planning containing information needed to meet specification requirements for an ultrasonic inspection, wherein said input data includes part geometry data and a revision sheet for said part;

calculating inspection parameters from said data; and formatting said calculated parameters into an inspection plan document.

22. The computer-readable medium of claim 21 wherein said instructions further cause a computer system to display an instruction screen.

23. The computer-readable medium of claim 21 wherein said instructions further cause a computer system to generate an error proofing plot of said part.

24. The computer-readable medium of claim 21 wherein calculating inspection parameters includes calculating one or more of part rotational speed, part surface speed, transducer index speed, pulse repetition rate and scan length.

25. The computer-readable medium of claim 21 wherein said inspection plan document sets forth a sequence of inspection scans for said part.

26. The computer-readable medium of claim 21 wherein said data further includes a flow line image and a scan line image for said part.

27. The computer-readable medium of claim 21 wherein said data further includes ultrasonic transducer characteristics.

28. The computer-readable medium of claim 21 wherein said data further includes a proposed sequence of inspection scans.

29. The computer-readable medium of claim 25 wherein said document further includes a flow line image, a scan line image, inspection limits and a revision history for said part.

30. A system for automatically generating an ultrasonic inspection planning for a part, said ultrasonic inspection planning containing information needed to meet specification requirements for an ultrasonic inspection, said system comprising:

means for displaying an input screen for prompting a user to input data relating to said part, said input screen including a section for receiving a revision sheet for said part;

means for calculating inspection parameters from said data; and means formatting said calculated parameters into an inspection plan document.

31. The system of claim 30 further comprising means for displaying an instruction screen.

32. The system of claim 30, further comprising means for generating an error proofing plot of said part.

33. The system of claim 30 wherein said means for calculating inspection parameters includes calculating one or more of part rotational speed, part surface speed, transducer index speed, pulse repetition rate and scan length.

34. The system of claim 30 wherein said inspection plan document sets forth a sequence of inspection scans for said part.

35. The system of claim 30 wherein said document further includes a flow line image, a scan line image, inspection limits and a revision history for said part.

36. The system of claim 34 wherein said input screen includes a section for receiving part geometry data for said part.

37. The system of claim 35 wherein said input screen includes a section for receiving a flow line image and a scan line image for said part.

38. The system of claim 35 wherein said input screen includes a section for receiving ultrasonic transducer characteristics.

39. The system of claim 35 wherein said input screen includes a section for receiving a proposed sequence of inspection scans.

* * * * *

UNITED STATES PATENT AND TRADEMARK OFFICE
CERTIFICATE OF CORRECTION

PATENT NO.   : 6,820,023 B1
DATED        : November 16, 2004
INVENTOR(S)  : Klassen et al.

It is certified that error appears in the above-identified patent and that said Letters Patent is hereby corrected as shown below:

Column 8,
Line 63, delete "pail" and insert therefor -- part --.

Signed and Sealed this

Fourth Day of October, 2005

JON W. DUDAS
*Director of the United States Patent and Trademark Office*

UNITED STATES PATENT AND TRADEMARK OFFICE
CERTIFICATE OF CORRECTION

PATENT NO. : 6,820,023 B1
DATED : November 16, 2004
INVENTOR(S) : Klassen et al.

It is certified that error appears in the above-identified patent and that said Letters Patent is hereby corrected as shown below:

Column 8,
Line 63, delete "pail" and insert therefor -- part --.

Column 10,
Line 16, delete "30" and insert therefor -- 34 --.
Line 19, delete "34" and insert therefor -- 30 --.
Lines 22 and 25, delete "35" and insert therefor -- 36 --.

Signed and Sealed this

Eighteenth Day of October, 2005

JON W. DUDAS
*Director of the United States Patent and Trademark Office*